United States Patent
Kim et al.

(10) Patent No.: US 7,294,371 B2
(45) Date of Patent: Nov. 13, 2007

(54) LIQUID CRYSTAL COMPOUND HAVING HIGH OPTICAL ANISOTROPY AND NEGATIVE DIELECTRIC ANISOTROPY, LIQUID CRYSTAL COMPOSITION INCLUDING THE SAME AND LIQUID CRYSTAL DISPLAY INCLUDING THE LIQUID CRYSTAL COMPOSITION

(75) Inventors: Jong-seob Kim, Gyeonggi-do (KR); Yoon-sok Kang, Gyeonggi-do (KR); Jee-hwan Jang, Gyeonggi-do (KR); Jong-min Wang, Gyeonggi-do (KR); Byung-soon Chen, Gyeonggi-do (KR)

(73) Assignee: Samsung Electronics Co., Ltd., Suwon-si, Gyeonggi-do (KR)

( * ) Notice: Subject to any disclaimer, the term of this patent is extended or adjusted under 35 U.S.C. 154(b) by 340 days.

(21) Appl. No.: 10/949,527

(22) Filed: Sep. 27, 2004

(65) Prior Publication Data

US 2005/0104039 A1 May 19, 2005

(30) Foreign Application Priority Data

Oct. 30, 2003 (KR) ............... 10-2003-0076213

(51) Int. Cl.
  *C09K 19/12* (2006.01)
  *C09K 19/30* (2006.01)
  *C07C 25/13* (2006.01)

(52) U.S. Cl. ............ 428/1.3; 252/299.63; 252/299.66; 570/129

(58) Field of Classification Search ............... 428/1.1, 428/1.3; 252/299.63, 299.66; 570/129
See application file for complete search history.

(56) References Cited

U.S. PATENT DOCUMENTS

| | | | | |
|---|---|---|---|---|
| 5,384,065 | A * | 1/1995 | Geelhaar et al. | 252/299.63 |
| 6,740,369 | B2 * | 5/2004 | Klasen-Memmer et al. | 428/1.1 |
| 6,764,722 | B2 * | 7/2004 | Klasen et al. | 428/1.1 |
| 2002/0014613 | A1 * | 2/2002 | Klasen et al. | 252/299.63 |
| 2003/0071244 | A1 * | 4/2003 | Klasen-Memmer et al. | 252/299.66 |

FOREIGN PATENT DOCUMENTS

| | | |
|---|---|---|
| JP | 2001-254967 | 12/2001 |
| KR | 10-2000-0054975 | 9/2000 |
| KR | 10-2000-0054976 | 9/2000 |

OTHER PUBLICATIONS

CAPLUS 1992: 245636.*
Klasen, Melanie et al., "New Liquid Crystal Materials for Active Matrix Displays With Negative Dielectric Anisotropy and Low Rotational Viscosity", *Japanese Journal of Applied Physics*, vol. 39 (2000), pp. 1180-1182.

* cited by examiner

*Primary Examiner*—Shean C. Wu
(74) *Attorney, Agent, or Firm*—Buchanan Ingersoll & Rooney PC

(57) ABSTRACT

Provided are a liquid crystal compound represented by formula 1, a liquid crystal composition including the same, and a liquid crystal display including the liquid crystal composition:

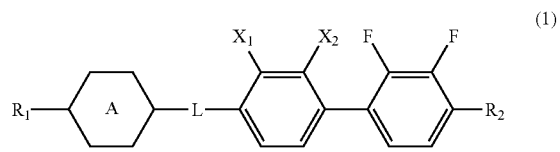

(1)

wherein $X_1$, $X_2$, $R_1$, $R_2$, L and

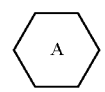

are the same as described in specification. High optical anisotropy and negative dielectric anisotropy can be achieved by the use of the liquid crystal composition including the liquid crystal compound.

18 Claims, No Drawings

LIQUID CRYSTAL COMPOUND HAVING HIGH OPTICAL ANISOTROPY AND NEGATIVE DIELECTRIC ANISOTROPY, LIQUID CRYSTAL COMPOSITION INCLUDING THE SAME AND LIQUID CRYSTAL DISPLAY INCLUDING THE LIQUID CRYSTAL COMPOSITION

This application claims the priority of Korean Patent Application No. 2003-76213, filed on Oct. 30, 2003, in the Korean Intellectual Property Office, the disclosure of which is incorporated herein in its entirety by reference.

BACKGROUND OF THE INVENTION

1. Field of the Invention

The present invention relates to a diphenyl based liquid crystal compound, a liquid crystal composition including the same, and a liquid crystal display including the liquid crystal composition, and more particularly, to a liquid crystal compound having high optical anisotropy and negative dielectric anisotropy, a liquid crystal composition including the same, and a liquid crystal display employing the liquid crystal composition.

2. Description of the Related Art

As the modern industrial society steps into the high information era, electronic displays are regarded as being more and more important for mass distribution of a variety of information. In particular, flat panel displays are highlighted by their advantages of lightweight, thin design, and their application to large size. As a result, flat panel displays are widely used in many fields such as monitors for laptop computers, aircraft controlling equipment, medical instruments, navigators, and measuring instruments. Types of flat panel displays include liquid crystal displays (LCDs), field emission displays (FEDs), plasma display panels (PDPs), and electro luminescent displays (ELDs). In particular, LCDs have been leading the market for the flat panel displays due to their advantages of portability and low power consumption.

The liquid crystal displays (LCDs) are divided into projection LDCs and direct-view LCDs, and the direct-view LCDs are divided into transmissive displays and reflective displays. In transmissive LCDs, the intensity of light emitted from backlight is controlled by LCD panels. In reflective LCDs, images are formed by reflection of natural light and surrounding light onto LCD panels. Among the reflective LCDs, liquid crystals on silicon microdisplays (LCoS) have recently drawn a lot of attentions.

Generally, a LCoS display includes a liquid crystal layer including a liquid crystal material interposed between a silicon substrate and a glass cover. The silicon substrate includes an array of pixels and each of them is conductive and reflective. Although the LCoS display has a screen size of smaller than 1 inch when measured diagonally, it can display a high resolution image. LCoS displays have a small pixel size. Therefore, in general, cell thickness is very small, even smaller than 1 micrometer. Therefore, a liquid crystal composition used in the LCoS display must have a very high optical anisotropy, as opposed to other LCDs in which a low optical anisotropy is usually sufficient.

Liquid crystal compounds used in VA mode LCDs, which use a Vertical Alignment (VA) technique should have high optical anisotropy and negative dielectric anisotropy. The liquid crystal compound must have a low K33/K11 (ratio of elastic constants) and rotation viscosity, and high chemical stability against external influences such as UV, heat, infrared light, air and electric fields. Also the liquid crystal compound must have a liquid crystal phase having a wide temperature range and rapid response speed.

Korean Patent Application No. 99-3372 discloses a liquid crystal composition including a liquid crystal compound, which is a cyclohexene derivative. The liquid crystal composition provides good optical anisotropy and positive dielectric anisotropy. In addition, Korean Patent Application No. 99-3373 also discloses a liquid crystal composition providing good optical anisotropy and positive dielectric anisotropy.

However, a single compound having high optical anisotropy and negative dielectric anisotropy is not well known. Attempts have been made to obtain both high optical anisotropy and negative dielectric anisotropy in a liquid crystal composition by mixing about 5-25 liquid crystal compounds. However, the attempts to manufacture an ideal liquid crystal phase having high optical anisotropy and negative dielectric anisotropy have failed. Accordingly, there is a need to develop a liquid crystal compound having high optical anisotropy and negative dielectric anisotropy and a liquid crystal composition including the compound.

SUMMARY OF THE INVENTION

The present invention provides a liquid crystal compound having high optical anisotropy and negative dielectric anisotropy.

The present invention also provides a liquid crystal composition including the liquid crystal compound having high optical anisotropy and negative dielectric anisotropy.

The present invention also provides a liquid crystal display employing the liquid crystal composition including the liquid crystal compound having high optical anisotropy and negative dielectric anisotropy.

According to an aspect of the present invention, there is provided a liquid crystal compound of formula 1:

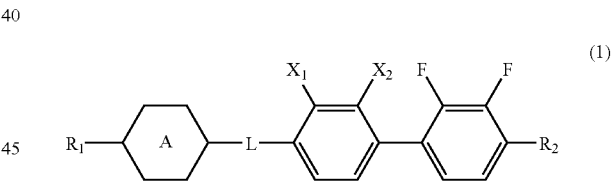

(1)

wherein each of $X_1$ and $X_2$ is independently selected from the group consisting of H, a halogen atom, NCS, CN, a $C_{1-5}$ alkyl group substituted with a halogen atom, and a $C_{1-5}$ alkoxy group substituted with a halogen atom;

each of $R_1$ and $R_2$ is independently selected from the group consisting of a $C_{1-20}$ alkyl group unsubstituted or substituted with a halogen atom, a $C_{2-20}$ alkenyl group unsubstituted or substituted with a halogen atom, a $C_{1-20}$ alkoxy group unsubstituted or substituted with a halogen atom, a $C_{2-20}$ alkenyloxy group unsubstituted or substituted with a halogen atom, a $C_{3-20}$ cycloalkyl group unsubstituted or substituted with a halogen atom, and a $C_{6-20}$ aryl group unsubstituted or substituted with a halogen atom;

L is a single bond or a linking group selected from the group consisting of a $C_{1-7}$ alkylene group, a $C_{2-7}$ alkenylene group, a $C_{2-7}$ alkynylene group, —COO—, —OCO—, —CH$_2$O—, —OCH$_2$—, —CF$_2$O—, —OCF$_2$—, —NHCH$_2$—, —CH$_2$NH—, —CH$_2$CO—, —COCH$_2$—, and —N=N—; and

is selected from the group consisting of

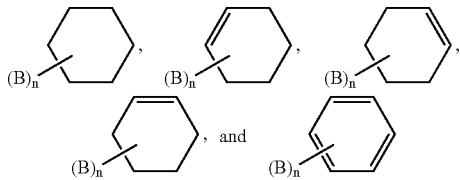

wherein B is H or a halogen atom and may be same to or different from each other, and n is an integer between 1 and 8.

The compound represented by formula 1 may be represented formula 2 or formula 3:

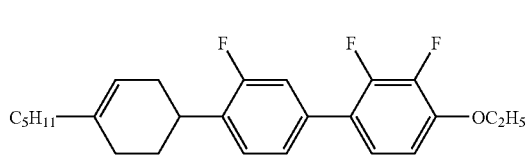

(2)

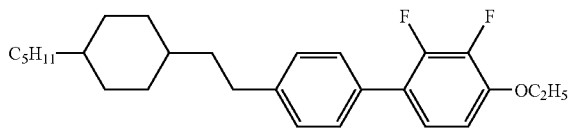

(3)

According to another aspect of the present invention, there is provided a liquid crystal composition including the compound represented by formula 1.

The liquid crystal composition may be a compound selected from a compound of formula 4, a compound of formula 5, a compound of formula 6, and a compound of formula 7:

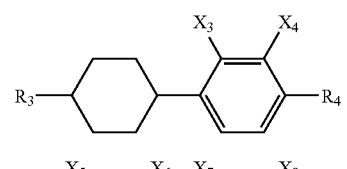

(4)

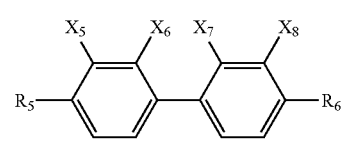

(5)

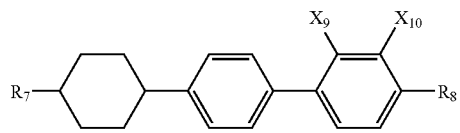

(6)

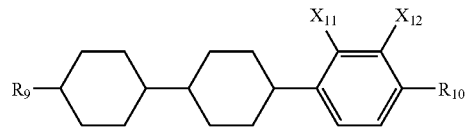

(7)

wherein each of $X_3$, $X_4$, $X_5$, $X_6$, $X_7$, $X_8$, $X_9$, $X_{10}$, $X_{11}$ and $X_{12}$ is independently one of H and a halogen atom and each of $R_3$, $R_4$, $R_5$, $R_6$, $R_7$, $R_8$, $R_9$ and $R_{10}$ is independently one of $C_{1-7}$ alkyl group and $C_{1-7}$ alkoxy group.

According to still another aspect of the present invention, there is provided a liquid crystal display including a liquid crystal layer disposed between a pair of electrode substrates, wherein the liquid crystal layer includes the liquid crystal composition.

Since the liquid crystal composition including the compound represented by formula 1 provides high optical anisotropy and negative dielectric anisotropy, the liquid crystal composition is suitable for a display using double refraction effect. Examples of the display using double refraction effect include a vertical alignment (VA) mode display, a liquid crystal on silicon (LCoS) mode display, and a reflective display.

DETAILED DESCRIPTION OF THE INVENTION

Hereinafter the present invention will now be described in detail.

According to a first aspect of the present invention, a liquid crystal compound is given by formula 1 below:

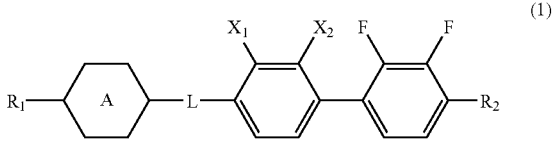

(1)

wherein each of $X_1$ and $X_2$ is independently selected from H, a halogen atom, NCS, CN, a $C_{1-5}$ alkyl group substituted with a halogen atom, and a $C_{1-5}$ alkoxy group substituted with a halogen atom;

each of $R_1$ and $R_2$ is independently a $C_{1-20}$ alkyl group unsubstituted or substituted with a halogen atom, a $C_{2-20}$ alkenyl group unsubstituted or substituted with halogen atom, a $C_{1-20}$ alkoxy group unsubstituted or substituted with a halogen atom, a $C_{2-20}$ alkenyloxy group unsubstituted or substituted with a halogen atom, a $C_{3-20}$ cycloalkyl group unsubstituted or substituted with a halogen atom, or a $C_{6-20}$ aryl group unsubstituted or substituted with a halogen atom;

L is a single bond or a linking group selected from a $C_{1-7}$ alkylene group, a $C_{2-7}$ alkenylene group, a $C_{2-7}$ alkynylene group, —COO—, —OCO—, —CH$_2$O—, —OCH$_2$—, —CF$_2$O—, —OCF$_2$—, —NHCH$_2$—, —CH$_2$NH—, —CH$_2$CO—, —COCH$_2$—, and —N═N—;

is selected from

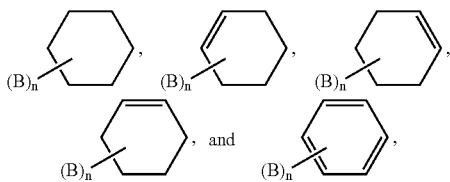

wherein B is H or a halogen atom and may be the same with or different from each other, and n is an integer between 1 and 8.

Each of $X_1$ and $X_2$ may be independently H or F.

Each of $R_1$ and $R_2$ may be independently a $C_{1-20}$ alkyl group unsubstituted or substituted with a halogen atom, a $C_{2-20}$ alkenyl group unsubstituted or substituted with a halogen atom, a $C_{1-20}$ alkoxy group unsubstituted or substituted with a halogen atom, and a $C_{2-20}$ alkenyloxy group unsubstituted or substituted with a halogen atom, and preferably, $R_1$ may be a propyl group or a pentanyl group and $R_2$ may be an ethoxy group.

L may be a single bond; or a $C_{1-4}$ alkylene group, a $C_{2-5}$ alkenylene group, or a $C_{2-5}$ alkynylene group, and preferably L is a single bond or an ethenylene group.

Examples of the unsubstituted $C_{1-20}$ alkyl group in formula 1 according to the present embodiment include methyl, ethyl, propyl, isobutyle, sec-butyl, pentyl, iso-armyl, and hexyl, but are not limited thereto.

Examples of the unsubstituted $C_{1-20}$ alkoxy group in formula 1 according to the present embodiment include methoxy, ethoxy, and buthoxy, but are not limited thereto.

A $C_{6-20}$ aryl group in formula 1 according to the present embodiment means a $C_{6-20}$ carbocycle aromatic system including at least one ring. If there is more than one, the rings can be attached to each other using a pendent method or fused with each other. The aryl group may include aromatic radicals such as, but not limited to, phenyl, naphthyl, and tetrahydronaphthyl.

The compound of formula 1 may be represented by formula 2:

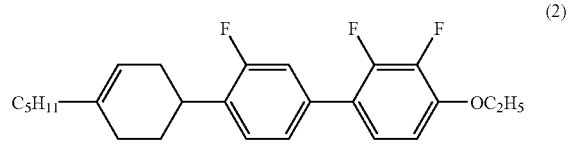

or formula 3:

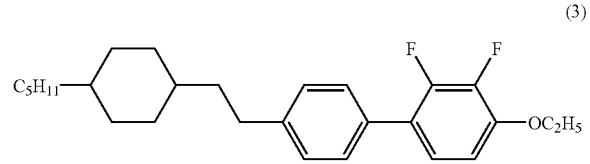

According to a second aspect of the present invention, a liquid crystal composition includes the compound of formula 1.

The liquid crystal composition may further includes at least one of a compound of formula 4, a compound of formula 5, a compound of formula 6, and a compound of formula 7:

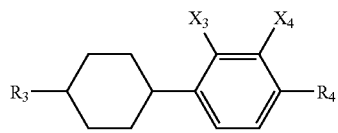

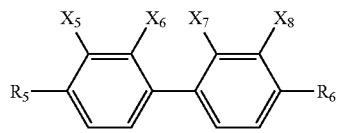

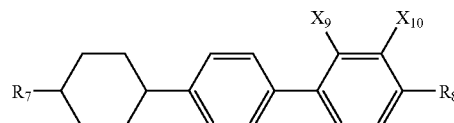

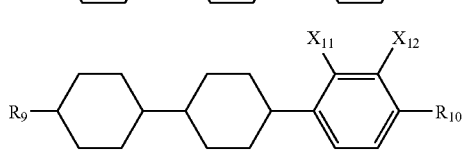

wherein each of $X_3, X_4, X_5, X_6, X_7, X_8, X_9, X_{10}, X_{11}$ and $X_{12}$ is independently H or a halogen atom;

each of $R_3, R_4, R_5, R_6, R_7, R_8, R_9$ and $R_{10}$ is independently a $C_{1-7}$ alkyl group or a $C_{1-7}$ alkoxy group.

Each of $X_3, X_4, X_5, X_6, X_7, X_8, X_9, X_{10}, X_{11}$ and $X_{12}$ may be independently H or F.

Each of $R_3, R_5, R_7$ and $R_9$ may be independently a prophyl group, a butyl group or a pentyl group, and each of $R_4, R_6, R_8$ and $R_{10}$ may be independently a methoxy group, an ethoxy group or a buthoxy group.

The compounds of formulas 4 through 7 can be further included in the liquid crystal composition, not only to provide high optical anisotropy and negative dielectric anisotropy, but also to ensure that other characteristics such as voltage holding ratio, $T_{NI}$, and threshold voltage are better than those found in conventional liquid crystal compositions.

The liquid crystal composition may include the compound of formula 4 in an amount of 30-250 parts by weight, the compound of formula 5 in an amount of 10-130 parts by weight, the compound of formula 6 in an amount of 30-250 parts by weight, and the compound of formula 7 in an amount of 10-130 parts by weight based on the total weight of the liquid crystal compound of formula 1. Preferably, the liquid crystal composition includes the compound of formula 4 in an amount of 60-140 parts by weight, the compound of formula 5 in an amount of 10-70 parts by weight, the compound of formula 6 in an amount of 60-170 parts by weight, and the compound of formula 7 in an amount of 10-70 parts by weight based on the total weight of the liquid crystal compound of formula 1.

If the total weight of liquid crystal compounds other than the liquid crystal compound of formula 1 is greater than that mentioned above, then the composition ratio of the compound of formula 1 may be too low to obtain the desired high optical anisotropy and negative dielectric anisotropy. On the other hand, if the total weight of liquid crystal compounds other than the liquid crystal compound of formula 1 is less than that mentioned above, then the amount ratio of the compound of formula 1 may be too high to achieve the desired characteristics of the liquid crystal composition while maintaining other characteristics such as high voltage holding ratio, high $T_{NI}$, low threshold voltage.

According to a third aspect of the present invention, an LCD includes a liquid crystal layer interposed between a pair of electrode substrates. The liquid crystal layer includes the liquid crystal composition. The LCD may use double reflection. The LCD may be a vertical alignment (VA) mode display, a liquid crystal on silicon (LCoS) display, and a reflective display.

The liquid crystal display includes the liquid crystal composition according to an embodiment of the present invention so that characteristics such as voltage holding ratio, $T_{NI}$, rapid response speed, and threshold voltage can be maintained while obtaining high optical anisotropy and negative dielectric ratio.

The present invention will be further described by present examples. These examples are for illustrative purpose only, and are not intended to limit the scope of the present invention.

EXAMPLE

Synthesis Example 1

Preparation of 4-ethoxy-2,3,3'-trifluoro-4'-(4-pentyl-cyclohex-3-enyl)-biphenyl (the Compound of Formula 2)

4-ethoxy-2,3,3'-trifluoro-4'-(4-pentyl-cyclohex-3-enyl)-biphenyl was prepared according to Reaction Scheme 1(composed of reaction schemes 1a and 1b).

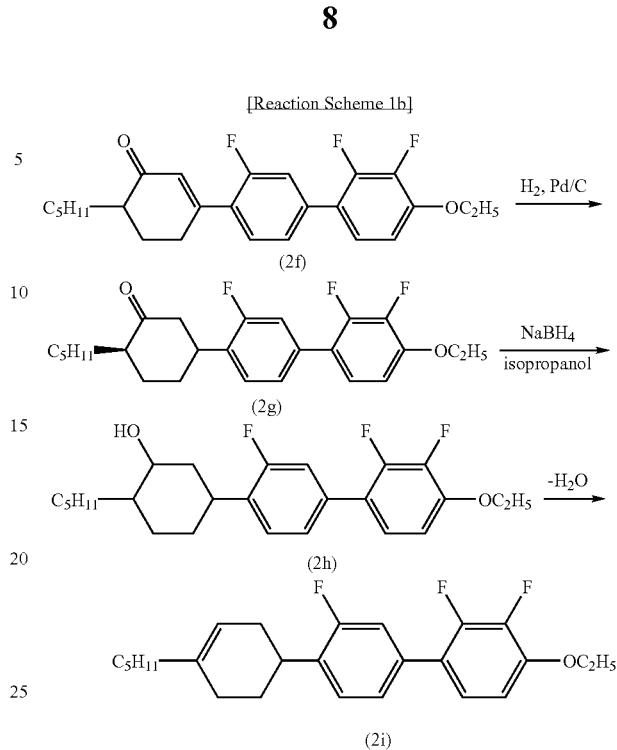

1. Synthesis of Compound (2b)

41.3 g (0.46 mol, 1.3 eq) of $AlCl_3$ was dissolved in 500 ml of methylene chloride and then the temperature of the

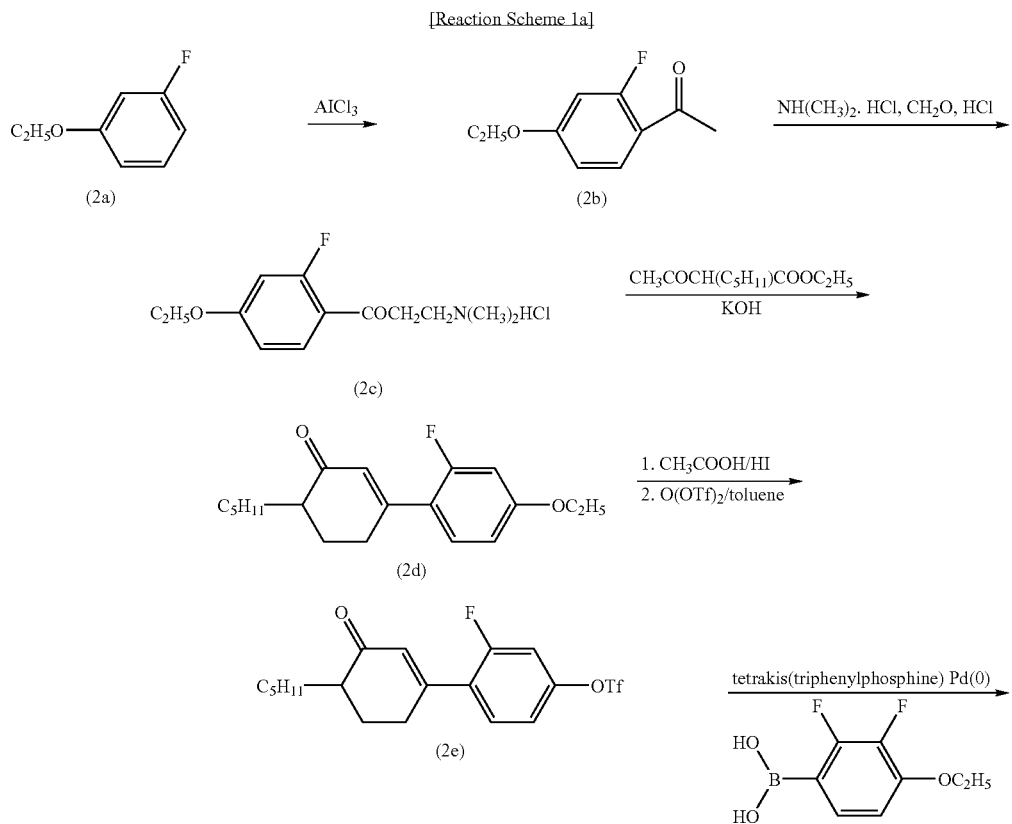

mixture was dropped to 5° C. 36.4 g (0.46 mol, 1.3 eq) of acetyl chloride was added to the mixture and then the temperature of the mixture was dropped to 0° C. A solution of 50 g (0.37 mol, 1.0 eq) of Compound (2a) in 50 ml of methylene chloride was slowly added to the mixture. The resulting mixture was stirred for 4 hours at room temperature, extracted using methylene chloride, washed with water and an 5% HCl aqueous solution, and dried using $MgSO_4$. The resultant was filtered to remove its solvent to prepare Compound (2b).

2. Synthesis of Compound (2c)

50 g (0.27 mol, 1.0 eq) of Compound (2b), 10.5 g (0.35 mol, 1.3 eq) of formaldehyde, 28.5 g (0.35 mol, 1.3 eq) of dimethylamine hydrochloride, and 20 ml of HCl in 300 ml of isopropanol was refluxed at 100° C. The refluxed solution was cooled to create a salt and then filtered to prepare Compound (2c).

3. Synthesis of Compound (2d)

35 g (0.13 mol, 1 eq) of Compound (2c) was dissolved in 400 ml of 1,4-dioxane. 25 g (0.44 mol, 3.5 eq) of KOH and 64 g (0.32 mol, 1.2 eq) of $CH_3COCH(C_5H_{11})COOC_2H_5$ were added to the mixture and refluxed at 105-110° C. The mixture was cooled and a 20% $H_2SO_4$ aqueous solution was added thereto. The resulting solution was extracted using ether, washed with water, and dried using $MgSO_4$. The resultant was filtered to remove its solvent to prepare Compound (2d).

4. Synthesis of Compound (2e)

100 ml of acetic acid and 100 ml of HI were added to 20 g (0.07 mol, 1.0 eq) of Compound (2d), and then refluxed for one day at 150° C. The reaction mixture was extracted using ether, washed with water, and dried using $MgSO_4$. The resultant was filtered and its solvent was removed to yield a compound. The compound was added to 200 ml of toluene and then 25.8 g (0.09 mol, 1.2 eq) of $(OTf)_2O$ was added thereto. The mixture was stirred for 3 hours at room temperature. The stirred mixture was extracted using ether, washed with water, and dried using $MgSO_4$. The resultant was filtered to remove its solvent to prepare Compound (2e).

5. Synthesis of Compound (2f)

15 g (0.038 mol, 1.0 eq) of Compound (2e) was dissolved in 50 ml of benzene, and then 1 g of tetrakis (triphenyl phosphine) Pd(0) was added thereto. 50 ml of 2M $Na_2CO_3$ was added to the resulting mixture and stirred. Then, a solution of 9.2 g (0.045 mol, 1.2 eq) of 2,3-difluoro-4-ethoxybenzeneboronic acid in 100 ml of ethanol was dripped into the mixture using a dropping funnel. The mixture was refluxed at 100° C. for 4 hours, extracted using toluene, washed with water, and dried using $MgSO_4$. The result was filtered to remove its solvent to prepare Compound (2f).

6. Synthesis of Compound (2g)

15 g of Compound (2f) was dissolved in 200 ml of toluene and 200 ml of ethanol, and then 1.5 g of 5% Pd/C was added thereto. Then, $H_2$ was added to the mixture at a pressure of 5 bar at 40° C., and stirred for one day. The catalyst (Pd/C) was removed from the reaction mixture using celite, and the solvent of the reaction mixture was removed to prepare Compound (2g)

7. Synthesis of Compound (2h)

5 g (0.012 mol, 1.0 eq) of Compound (2g) was dissolved in 50 ml of isopropanol, and then 0.54 g (0.014 mol, 1.2 eq) of $NaBH_4$ was added thereto. The mixture was stirred at room temperature for 4 hours. The reaction mixture was extracted using ether, washed with water, and then dried using $MgSO_4$. The result was filtered to remove its solvent to thereby prepare Compound (2h).

8. Synthesis of Final Compound (2i)

5 g of Compound (2h) was dissolved in toluene, and then 0.5 g of p-toluenesulfonic acid was added thereto. The mixture was refluxed at 130° C. for 4 hours. The reaction mixture was extracted using ether, washed with an $Na_2CO_3$ aqueous solution, and dried using $MgSO_4$. The dried mixture was filtered to remove its solvent to prepare Compound (2i) (the compound of formula 2). The results of gas chromatograpy-mass spectrometry (GC-MS) analysis are as follows: GC-MS peak analysis of Final Compound (2i): 402(M+)/278/265/250/237/219/201.

Synthesis Example 2

Preparation of 4-ethoxy-2,3-difluoro-4'-[2-(4-pentyl-cyclohexyl)-ethyl]-biphenyl (the Compound of Formula 3)

4-ethoxy-2,3-difluoro-4'-[2-(4-pentyl-cyclohexyl)-ethyl]-biphenyl was prepared according to Reaction scheme 2 (composed of Reaction schemes 2a and 2b)

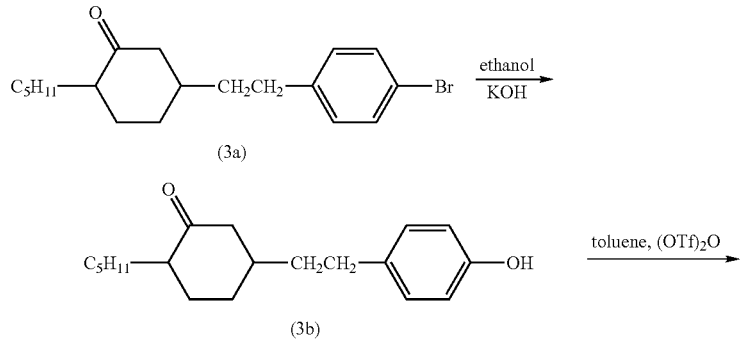

-continued

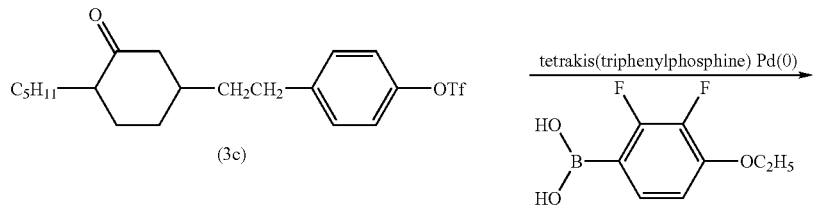

(3c)

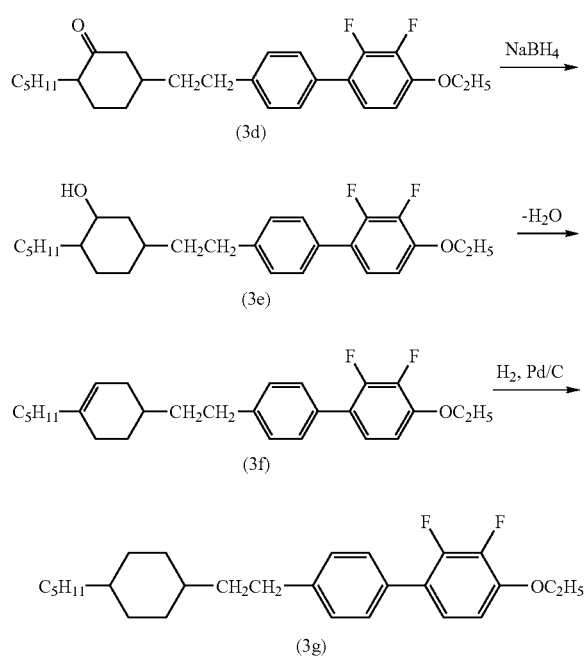

[Reaction Scheme 2b]

1. Synthesis of Compound (3b)

20 g (0.06 mol. 1.0 eq) of Compound (3a) was dissolved in 200 ml of ethanol, and then 4.8 g (0.085 mol, 1.5 eq) of KOH was added thereto. The mixture was refluxed at 100° C. for 4 hours. The reaction mixture was extracted using ether, washed with water and a 5% HCl aqueous solution, and dried using MgSO₄. The resultant was filtered to remove its solvent to prepare Compound (3b).

2. Synthesis of Compound (3c)

15 g (0.05 mol, 1.0 eq) of Compound (3b) was added to 100 ml of toluene, and then 17.6 g (0.062 mol, 1.2 eq) of (OTf)₂O was added thereto. The mixture was stirred at room temperature for 3 hours. The reaction mixture was extracted using ether, washed with water, and dried using MgSO₄. The resultant was filtered to remove its solvent to prepare Compound (3c).

3. Synthesis of Compound (3d)

15 g (0.035 mol, 1.0 eq) of Compound (3c) was dissolved in 50 ml of benzene, and then 1 g of tetrakis(triphenylphosphine)Pd(0) was added thereto. Then, 50 ml of 2M Na₂CO₃ was added to the mixture and stirred. Then, a solution of 8.63 g (0.042 mol, 1.2 eq) of 2,3-difluoro-4-ethoxybenzeneboronic acid in 100 ml of ethanol was dripped into the resulting mixture using a dropping funnel. The reaction mixture was refluxed at 100° C. for 4 hours, extracted using toluene, washed with water, and dried using MgSO₄. The resultant was filtered to remove its solvent to thereby prepare Compound (3d).

4. Synthesis of Compound (3e)

5 g (0.0116 mol, 1.0 eq) of Compound (3d) was dissolved in 50 ml of isopropanol, and then 0.53 g (0.014 mol, 1.2 eq) of NaBH₄ was added thereto. The mixture was stirred at room temperature for 4 hours. The reaction mixture was extracted using ether, washed with water, and dried using MgSO₄. The resultant was filtered to remove its solvent to prepare Compound (3e).

5. Synthesis of Compound (3f)

5 g of Compound (3e) was dissolved in 50 ml of toluene, and then 0.5 g of p-toluenesulfonic acid was added thereto. The mixture was refluxed at 130° C. for 4 hours. The reaction mixture was extracted using ether, washed with a Na₂CO₃ aqueous solution, and dried using MgSO₄. The result was filtered to remove its solvent to prepare Compound (3f).

6. Synthesis of Final Compound (3g)

4.3 g of Compound (3f) was dissolved in 100 ml of toluene and 100 ml of ethanol, and then 0.4 g of 5% Pd/C was added thereto. Then, H₂ was added to the mixture at a pressure of 5 bar at 40° C., and then stirred for one day. Then, the catalyst (Pd/C) was removed from the reaction mixture using celite, and then the solvent of the reaction mixture was removed to prepare Compound (3g) (the compound of formula 3). The results of gas chromatography-mass spectrometry analysis of Compound (3g) are as follows: GC-MS peak analysis data of Compound (3g): 414 (M+)/247/232/219.

Preparation Example

Preparation of Liquid Crystal Composition

Liquid crystal compounds of Table 1 were mixed according to the indicated weight ratios, heated to an isotropic phase, and then cooled to room temperature, thus being in a nematic phase. This heating/cooling process was repeated until the liquid crystal compounds were completely mixed to prepare a liquid crystal composition according to the present invention.

TABLE 1
Components of a liquid crystal composition and weight ratio of each component. (Unit % by weight)
| Formula No. | Compound | composition ratio |
|---|---|---|
| 4 | 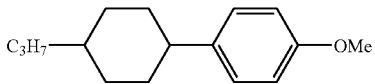 | 2 |
|  | 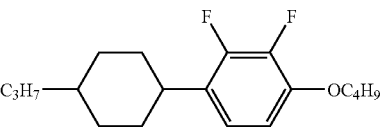 | 6 |
|  | 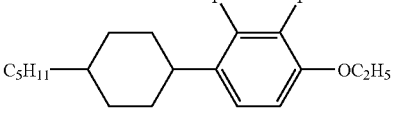 | 6 |
|  | 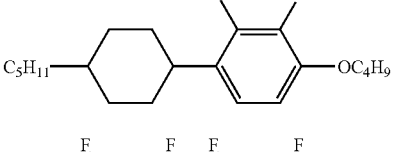 | 10 |
| 5 | 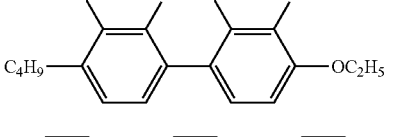 | 6 |
| 6 | 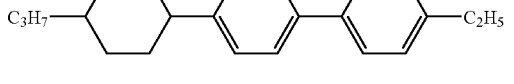 | 7 |
|  | 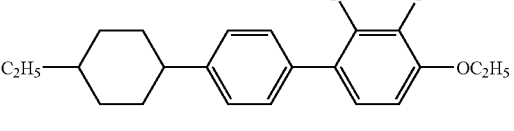 | 14 |
|  | 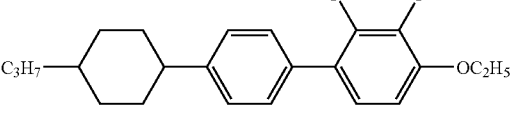 | 12 |
| 7 | 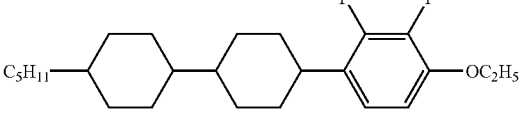 | 4 |
|  | 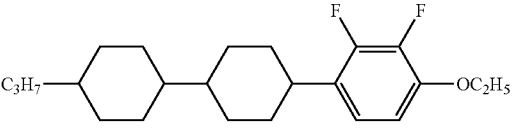 | 3 |
| 2 | 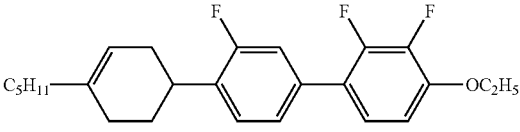 | 15 |

TABLE 1-continued

Components of a liquid crystal composition and weight ratio of each component. (Unit % by weight)

| Formula No. | Compound | composition ratio |
|---|---|---|
| 3 | 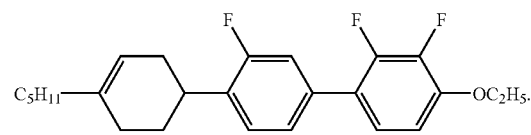 | 15 |

Example

Measurements of Electro-optical Characteristic of Liquid Crystal Composition Dielectric anisotropy of perpendicularly-arranged liquid crystal cells in which the liquid crystal composition of Preparation Example was injected thereto was measured using Model 6254 (obtained form Toyo Corporation) at 0.1 Hz and 20° C. In addition, reflective indexes for ordinary light and not-ordinary light were measured at 20° C. using an Abbe refractometer and a 589 nm interference filter, to measure optical anisotropy of the liquid crystal composition. Maintaining the heating rate and the cooling rate at 2° C./min, the phase transition temperature was measured using a polarization microscope to which a hot stage was included.

Parameters related to the electro-optical characteristic are represented in Table 2:

TABLE 2

| Parameters for the measurement of electro-optical characteristic | |
|---|---|
| Physical property | Unit |
| Optical anisotropy ($\Delta n$) at 20° C., 589 nm | |
| Dielectric anisotropy ($\Delta \epsilon$) at 20° C., 0.1 Hz | |
| Nematic anisotropy transition temperature ($T_{NI}$) | ° C. |

These measured electro-optical characteristics of the liquid crystal composition of Preparation Examples are presented below.

Optical anisotropy ($\Delta n$): 0.15
Dielectric anisotropy ($\Delta \epsilon$): −4.9
Nematic anisotropy transition temperature ($T_{NI}$): 98.6° C.

Therefore, the optical anisotropy, the dielectric anisotropy, and the nematic anisotropy transition temperature of the liquid crystal composition according to the present invention are suitable for VA mode liquid crystal displays. In particular, the performance of the liquid crystal composition according to the present invention is far superior to that of a VA mode high optical anisotropy liquid crystal compound of Merck Ltd., which has recently been presented by Klasen-Memmer at the 7th Merck Liquid Crystals Seminar 2003. The VA mode high optical anisotropy liquid crystal compound has a dielectric anisotropy of 3.7, an optical anisotropy of 0.127, and a nematic anisotropy transition temperature of 80.0° C.

The liquid crystal composition including the liquid crystal compound according to the present invention has desired properties. That is, a high voltage holding ratio, high $T_{NI}$, rapid response speed, and low threshold voltage can be maintained while achieving high optical anisotropy and negative dielectric anisotropy. Even though both high optical anisotropy and negative dielectric anisotropy are necessary requirements for liquid crystal displays, particularly for LCoS mode displays or VA mode displays, no conventional liquid crystal composition has been reported having all of the parameters mentioned with in desirable range. Therefore, a liquid crystal compound according to the present invention and an liquid crystal composition including the same are very useful for, in particular, LCDs.

What is claimed is:
1. The liquid crystal compound represented by the following formula:

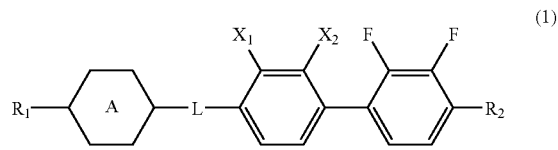

2. A liquid crystal composition comprising the liquid crystal compound of formula 1 below:

wherein each of $X_1$ and $X_2$ is independently selected from the group consisting of H, a halogen atom, NCS, CN, a $C_{1-5}$ alkyl group substituted with a halogen atom, and a $C_{1-5}$ alkoxy group substituted with a halogen atom;
each of $R_1$ and $R_2$ is independently selected from the group consisting of a $C_{1-20}$ alkyl group unsubstituted or substituted with a halogen atom, a $C_{2-20}$ alkenyl group unsubstituted or substituted with a halogen atom, a $C_{1-20}$ alkoxy group unsubstituted or substituted with a halogen atom, a $C_{2-20}$ alkenyloxy group unsubstituted or substituted with a halogen atom, a $C_{3-20}$ cycloalkyl group unsubstituted or substituted with a halogen atom, and a $C_{6-20}$ aryl group unsubstituted or substituted with a halogen atom;

L is a single bond or a linking group selected from the group consisting of a $C_{1-7}$ alkylene group, a $C_{2-7}$ alkenylene group, a $C_{2-7}$ alkynylene group, —COO—, —OCO—, —CH$_2$O—, —OCH$_2$—, —CF$_2$O—, —OCF$_2$—, —NHCH$_2$—, —CH$_2$NH—, —CH$_2$CO—, —COCH$_2$—, and —N═N—; and

is selected from the group consisting of

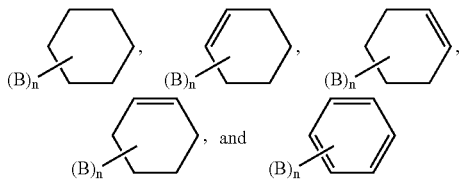

wherein B is H or a halogen atom and may be the same with or different from each other, and n is an integer between 1 and 8, further comprising a compound of formula 4, a compound of formula 5, a compound of formula 6, and a compound of formula 7:

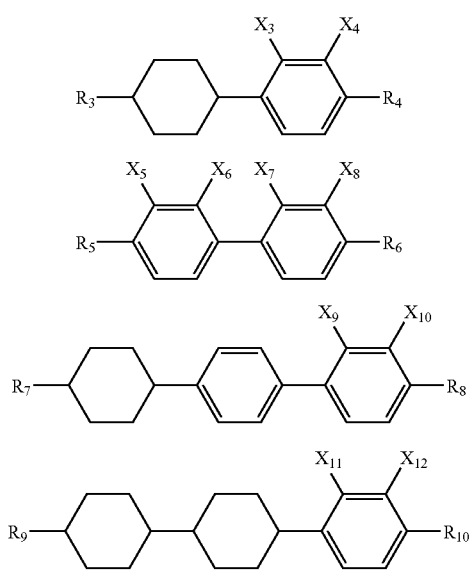

wherein each of $X_3$, $X_4$, $X_5$, $X_6$, $X_7$, $X_8$, $X_9$, $X_{10}$, $X_{11}$ and $X_{12}$ is independently one of H and a halogen atom and each of $R_3$, $R_4$, $R_5$, $R_6$, $R_7$, $R_8$, $R_9$ and $R_{10}$ is independently one of $C_{1-7}$ alkyl group and $C_{1-7}$ alkoxy group, wherein the compound of formula 4 is present in an amount of 30-250 parts by weight, the compound of formula 5 is present in an amount of 10-130 parts by weight, the compound of formula 6 is present in an amount of 30-250 parts by weight, and the compound of formula 7 is present in an amount of 10-130 parts by weight based on the total weight of the liguid crystal compound of formula 1.

3. The liquid crystal composition of claim 2, wherein the liquid crystal compound of formula 1 is:

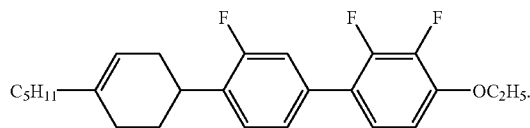

4. The liquid crystal composition of claim 2, wherein the liquid crystal composition of formula 1 is:

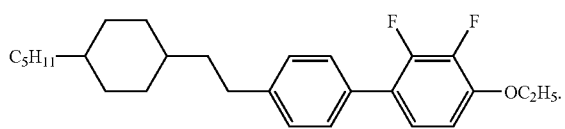

5. The liquid crystal composition of claim 2, wherein optical anisotropy is equal to or greater than 0.14.

6. The liquid crystal composition of claim 2, wherein dielectric anisotropy is smaller than −3.0.

7. A liquid crystal display comprising a liquid crystal layer interposed between a pair of electrode substrates, the liquid crystal layer comprising the liquid crystal composition of claim 2.

8. The liquid crystal display of claim 7, wherein the liquid crystal display is one of a LCoS mode liquid crystal display and a VA mode liquid crystal display.

9. A liquid crystal display comprising a liquid crystal layer interposed between a pair of electrode substrates, the liquid crystal layer comprising the liquid crystal composition of claim 3.

10. A liquid crystal display comprising a liquid crystal layer interposed between a pair of electrode substrates, the liquid crystal layer comprising the liquid crystal composition of claim 4.

11. A liquid crystal display comprising a liquid crystal layer interposed between a pair of electrode substrates, the liquid crystal layer comprising the liquid crystal composition of claim 5.

12. A liquid crystal display comprising a liquid crystal layer interposed between a pair of electrode substrates, the liquid crystal layer comprising the liquid crystal composition of claim 6.

13. The liquid crystal composition of claim 2, wherein the compound of formula 4 is present in an amount of 60-140 parts by weight, the compound of formula 5 is present in an amount of 10-70 parts by weight, the compound of formula 6 is present in a concentration of 60-170 parts by weight, and the compound of formula 7 is present in an amount of 10-70 parts by weight based on the total weight of the liquid crystal compound of formula 1.

14. A liquid crystal display comprising a liquid crystal layer interposed between a pair of electrode substrates, the liquid crystal layer comprising the liquid crystal composition of claim 13.

15. The liquid crystal composition of claim 13, wherein the liquid crystal compound of formula 1 is:

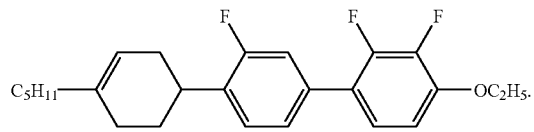

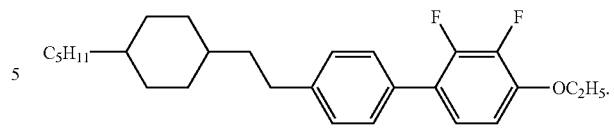

16. A liquid crystal display comprising a liquid crystal layer interposed between a pair of electrode substrates, the liquid crystal layer comprising the liquid crystal composition of claim 15.

17. The liquid crystal composition of claim 13, wherein the liquid crystal compound of formula I is:

18. A liquid crystal display comprising a liquid crystal layer interposed between a pair of electrode substrates, the liquid crystal layer comprising the liquid crystal composition of claim 17.

* * * * *